United States Patent
Lorenz et al.

(10) Patent No.: US 8,764,809 B2
(45) Date of Patent: Jul. 1, 2014

(54) TROCHANTER RETENTION PLATE

(75) Inventors: Kai-Uwe Lorenz, Speicher (CH); Heiko Durst, Speicher (CH); Markus Kuster, St. Gallen (CH)

(73) Assignee: SwissMedtechSolutions AG (CH)

( * ) Notice: Subject to any disclaimer, the term of this patent is extended or adjusted under 35 U.S.C. 154(b) by 258 days.

(21) Appl. No.: 12/377,502

(22) PCT Filed: Jul. 16, 2007

(86) PCT No.: PCT/CH2007/000344
§ 371 (c)(1),
(2), (4) Date: Apr. 6, 2009

(87) PCT Pub. No.: WO2008/019511
PCT Pub. Date: Feb. 21, 2008

(65) Prior Publication Data
US 2010/0234896 A1 Sep. 16, 2010

(30) Foreign Application Priority Data
Aug. 15, 2006 (CH) ..................................... 1309/06

(51) Int. Cl.
*A61B 17/80* (2006.01)
(52) U.S. Cl.
USPC ........... 606/286; 606/282; 606/283; 606/284; 606/285; 606/74
(58) Field of Classification Search
USPC ............ 606/74, 281, 283, 284, 286, 280, 282
See application file for complete search history.

(56) References Cited

U.S. PATENT DOCUMENTS

| | | | | |
|---|---|---|---|---|
| 5,261,908 A | * | 11/1993 | Campbell, Jr. | 606/279 |
| 5,702,399 A | | 12/1997 | Kilpela et al. | |
| 5,797,916 A | * | 8/1998 | McDowell | 606/74 |
| 6,066,141 A | * | 5/2000 | Dall et al. | 606/74 |
| 2004/0097942 A1 | | 5/2004 | Allen et al. | |
| 2006/0058795 A1 | * | 3/2006 | Boyd | 606/69 |
| 2006/0217722 A1 | * | 9/2006 | Dutoit et al. | 606/69 |

FOREIGN PATENT DOCUMENTS

| | | |
|---|---|---|
| DE | 102 26 074 A1 | 1/2003 |
| EP | 0 847 730 | 6/1998 |
| EP | 09 55 013 | 5/1999 |

OTHER PUBLICATIONS

International Search Report dated Nov. 16, 2007, issued in corresponding international application No. PCT/CH2007/000344.

* cited by examiner

*Primary Examiner* — Andrew Yang
*Assistant Examiner* — Olivia C Chang
(74) *Attorney, Agent, or Firm* — Ostrolenk Faber LLP

(57) ABSTRACT

The present disclosure relates to an implant for refixation of the greater trochanter on which an osteotomy has been performed or which is fractured. The implant comprises a plate that can be fixed on the proximal femur, and a device that can hold the greater trochanter with a form fit or force fit on the femur. This holding device preferably has bendable prongs located at a distance from each other, the first end portion of these prongs being attached to the upper edge of the base plate. The holding device also has flexible, elongate members, each of which is attached at one end to the free end portion of the respective prong. The other, free end portions of the longitudinal members are secured laterally on the base plate after these longitudinal members have crossed the medial aspect of the greater trochanter. This results in a tensioning band construction with at least two restraints based on a plate fixed securely on the proximal lateral femur.

12 Claims, 11 Drawing Sheets

TROCHANTER RETENTION PLATE

CROSS REFERENCE TO RELATED APPLICATIONS

The present application is a 35 U.S.C. §371 National Phase conversion of PCT/CH2007/000045, filed Jul. 16, 2007, which claims benefit of Swiss Application No. 1309/06, filed Aug. 15, 2006, the disclosure of which is incorporated herein by reference. The PCT International Application was published in the German language.

BACKGROUND

1. Field of the Disclosure

The present invention relates to an implant for the refixation of the osteotomised or fractured trochanter major (greater trochanter), to a so-called trochanter retention plate, and to a method for the operative refixation of the osteotomised or fractured trochanter major, with a trochanter retention plate.

2. Related Art

Various access paths to the hip joint, amongst other things, with osteotomy and subsequent refixation of the trochanter major, have been developed since the widespread introduction of hip endoprosthetics in the fifties and sixties. The refixation of this important tendon for the musculus gluteus medius and musculus gluteus minimus as well as different outer rotators should be effected in an anatomical manner after the prosthesis implantation. Moreover, the refixation of this important tendon should withstand the tensile force of the abductors, which under certain circumstances may amount to threefold the body weight. Various techniques have been developed for this purpose. Amongst these are for example the cerclage techniques which function with wires or cables. These may be supplemented by additional implants. These designs achieve reposition and compression of the present fragments by way of tension banding/cerclage, over the osteotomy location/fracture location. An actual neutralisation of the abductor tension is effected either via a type of braces-cerclage, which is fixed on the proximal femur, or not at all. The implants serve for the fixation of the wires/cables on the cranial-lateral aspect of the trochanter major. A direct, stable fixation of the implants on the proximal femur is not effected.

A further technique uses plate-like implants having a tension band function, which are fixed with screws or cerclages on the lateral aspect of the proximal femur. The reposition and fixation of the trochanter major is effected mostly via prong-like run-outs of the plate-like implants, which either only hook into the trochanter or which run out in an arched manner over the trochanter. A fixation in the trochanter region is effected either only with prongs or with cerclages around the trochanter massif (calcar femoris), or with screws into the trochanter-major-fragment. The laterally lying plate-like implants which exclusively take up the load, require a stable, partly high-profile design, in order to withstand the abductor forces. The lateral position directly above the tuberculum innominatum may then lead to the irritation of the tractus iliotibialis, which must slide over this region. Moreover, with larger radii or with a course of the prong around the trochanter-major-fragment, there exists the danger of the arch-like prongs bending open, or, with osteoporotic bones, of the partly sharp-edged prongs cutting in. Another technique makes the use of implants which are fixed directly on the prosthesis body, on the intramedullary nail or on the dynamic hip screw (DHS). Many of the mentioned implants have not displayed an adequate stability in clinical and/or biomechanical studies, or many of the mentioned implants suffered material failure in the course of dynamic loading.

SUMMARY

It is therefore the object of the present invention to provide an implant for the refixation of the osteotomised or fractured trochanter major, which avoids the disadvantages of the known implants.

It is moreover the object of the present invention to provide a method for implanting an implant for the refixation of the osteotomised or fractured trochanter major, which avoids the disadvantages of the known methods.

These objects are achieved by a trochanter retention plate according to the independent patent claim 1, and by a method according to the independent patent claim 9.

Trochanter retention plates according to the present invention permit the neutralisation of abductor forces, without significantly cutting into the bone substance of the trochanter major. This is significantly advantageous, in particular when osteoporosis is present.

The term plate in the description and the claims of the present invention is to include plates in the narrower sense, but also plate-like designs, for example reinforced [interwoven] fabrics of different, suitable materials, or plates of several parts which are actively connected to one another.

Suitable materials for plates, screws, bolts, cables, bands of the implant or of the trochanter retention plate according to the present invention are preferably selected from the group of stainless steel, stainless steel alloys, titanium, titanium alloys, medical plastics, carbon, Kevlar, composite materials or bioresorbable materials. The latter have the advantage that an operation for removal is done away with, but do not have an adequate stability for many applications. Different combinations of the above mentioned materials are possible and advantageous. Thus for example the distal plate shank may be designed in a rigid manner and the at least one proximal plate prong may be designed in a flexible manner, by way of the selection of different suitable materials.

According to preferred embodiments, the plate is designed in a solid manner or of a fabric which is likewise reinforced. The plate may also consist of a combination of solid or fabric (interwoven) components, so that as already indicated above, the material properties such as the elasticity for example, may be locally modified. The porosity of the plate material may likewise be modified in regions, which likewise permits an adaptation of local properties such as the strength and/or the elasticity for example.

BRIEF DESCRIPTION OF THE DRAWINGS

Embodiments of the invention are explained hereinafter in more detail by way of the attached drawings. There are shown in.

DETAILED DESCRIPTION OF THE EMBODIMENTS

Figure 2:
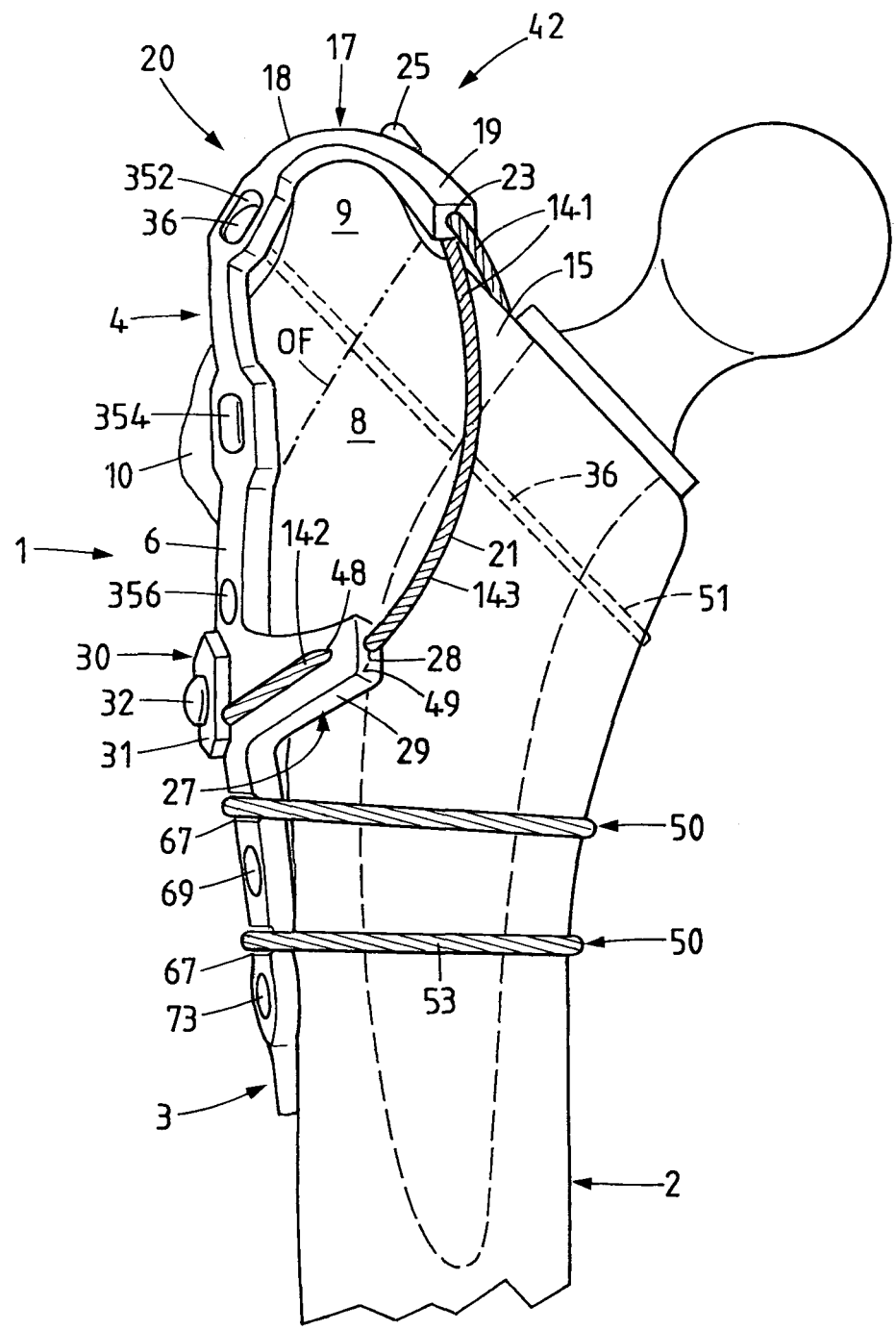
FIG. 2 the implant according to FIG. 1, in a lateral view.

The trochanter retention plate which, as above and in the following, is also called implant for short, amongst other things serves for the anatomical reposition and stable fixation of the trochanter major 9 on the proximal femur 2 after osteotomy or fracture. An osteotomy plane or fracture plane of the trochanter major fragment is indicated in FIG. 2 at OF. The shown plane corresponds essentially to a standard osteotomy. With total osteotomy, the osteotomy line would define a plane, which, with an approximately equal starting point, would be led further distally. With a so-called extended trochanteric osteotomy (ETO), the osteotomy line would be led yet essentially further distally up to into the proximal femur.

In the shown embodiment example, the present invention is realised based on a tension band principle, with two retainers, which results from a combination of a laterally lying plate and medially lying retainers.

The implant according to a first embodiment of the invention comprises a base plate 1 (FIGS. 1 and 2) which in the shown case is assigned to the lateral proximal femur 2. The base plate 1 is essentially flat and it may thus be arranged easily below the musculus vastus lateralis and around the tuberculum innominatum 10. The base plate 1 comprises a lower section 3, i.e. distant to the upper end of the femur 2, as well as an upper section 4, i.e. one lying closer to the upper end of the femur 2.

The upper section 4 of the base plate 1 comprises a surfaced main part 5 which is arched in an elongate manner. The longitudinal axis of this arching coincides with the longitudinal axis of the curvature of the outer surface of the femur 2, or it runs at least parallel thereto. The course of the curvature of this upper section 4 of the base plate 1 should correspond to the course of the curvature of the surface of that section of the femur 2, to which this section 4 of the base plate 4 is to be assigned. It is to be understood that the radius of the curvature of this section 4 of the base plate 1, may change along its practically vertically running longitudinal axis, depending on how the curvature of the surface of the femur 2 changes in its longitudinal direction. The base plate 1 furthermore comprises two narrow limbs 6 and 7 which are located at a distance to one another and which at one end connect to the upper edge 39 of the upper section 4 of the base plate 1 and depart from this edge 37. The limbs 6 and 7 are of one piece with the upper section 4 of the base plate 1, and they extend upwards from the upper section 4 of the base plate 1. The respective limb 6 and 7 lies ventrally or dorsally of the tuberculum innominatum 10. The limbs 6 and 7 have base bodies 11 and 12 running in an essentially arch-shaped manner and they are arranged convexly to one another. The base plate 1 also comprises a surfaced web 13, which is connected to the upper free end portions of the limbs 6 and 7 via its lower edge. The web 13 bridges these end portions of the limbs 6 and 7 and it mechanically connects them to one another. The two limbs 6 and 7 are thus connected to one another proximally of the tuberculum innominatum 10 by way of the web 13.

The upper edge portion 39 of the base body 5 of the upper plate section 4, as well as the inner edges of the limbs 6 and 7 and of the web 13, delimit an opening 14 in the base plate 1, which has a practically oval outline. The tuberculum innominatum 10 may lie in this opening 14 when the implant is attached on the femur 2. The limbs 6 and 7 thus bypass the tuberculum innominatum 10, so that the tractus iliotibialis may slide without problem or hindrance.

The proximal region 4 of the base plate 1 comprises four elongate holes 351, 352, 353 and 354, through which screws 36 pass, with whose help the base plate 1 may be fastened on the bone 2. In each case, two of these elongate holes 351 and 353, and 352 and 353, are designed in one of the limbs 6 and 7 respectively, of the base plate 1, and specifically at a vertical distance to one another. The first elongate hole 351 and 352 of the respective hole pair lies where the limb 6 and 7 respectively meets the web 13. The second elongate hole 353 and 354 of the respective hole pair is located roughly in the middle of the length of the limb 6 and 7 respectively, of the base plate 1. The longitudinal axis of the elongate holes 351 to 354 is aligned in a caudal-medial manner.

The base plate 1 is fastened on the proximal femur 8 with the help of screws 36, which pass through the holes 351 to 354. These screws 36 may merely go through the surface of the bone 2, or they may be designed so long, that they go through the trochanter fragment 9, or that the front region 51 of the threaded bolt of the screw 36, is screwed in the proximal femur 8 (FIG. 2). In the case that such a screw 36 goes through the trochanter fragment 9, without the thread of the screw bolt engaging with the material of the trochanter fragment 9, then one calls such a screw a tension screw.

The alignment of the screw holes 351 to 354 in combination with their elongate hole shape, permit an acute position of the screws 36 which is directed in a caudal-medial manner, in order to fix the trochanter fragment 9 over the osteotomy or fracture plane OF. When required, these screws 36 may be incorporated in the base plate 1 in an angularly stable manner. This means that the lower side of the head of the screw 36 is designed in a conical manner, and that the outer surface of this head section is provided with a thread. It is useful to design the side surfaces of the recesses 351 to 354 in the base plate 1 in a conical or tapering manner, so that the recesses 352 to 354 have obliquely running flanks. The material of the head of the screw 36 is harder than the material of the base plate 1, so that the thread on the conical section of the screw head cuts into the material of the base plate 1 on screwing-in the screw 26, and by way of this ensures an unchangeable angular position of the screw 36 with respect to the base plate 1. Such a connection between the respective portion of the base plate 1 and of the screw 36 may withstand alternating loads also over long time durations.

The trochanter fragment 9 may be fixed onto the proximal region 4 of the base plate 1, if a direct screwing is not possible. Thereby, the use of the mentioned angularly stable screw 36 is advantageous. A further two holes 355 and 356 are designed in the upper edge region 39 of the main part 5 of the proximal section 4. In each case, of one these holes 355 and 356 is located where the limbs 6 and 7 coincide with this upper edge region 39 of the main part 5 of the proximal section 4 of the base plate 1. Screws 36 may also be led through these holes 355 and 356, and be screwed in the proximal femur 2.

The implant further comprises a device for the non-positive retention of the trochanter major 9 on the femur 2. This holding device 20 in the represented case comprises two essentially flexible retainers 41 and 42. The respective retainer 41 and 42 comprises a strip-like prong 16 and 17 respectively. These prongs 16 and 17 are located at a distance to one another. The prongs 16 and 17 depart proximally of the web 13 and they are designed such that they may be adapted to the anatomy of the trochanter major. For this purpose, the complete prong 16 and 17, or at least a region 43 of the respective prong 16 and 17, is designed in a flexible manner. The flexible prongs 16 and 17 have an arched course, wherein this arch is directed upwards. One may thus say that the prongs 16 and 17 are pre-bent in a hook shape. For this reason, the trochanter fragment 9 is well encompassed or gripped in a proximal manner, and a good reposition of the trochanter fragment 9 may be achieved amid manual pulling. In order to keep the cutting of the prongs 16 and 17 into the trochanter major fragment as small as possible, the prongs 16 and 17 should be designed significantly wider than high. The prongs 16 and 17 may thus also be designed such that the stiffness of the respective prong 16 and 17 reduces with an increasing distance to the web 13, so that the prongs 16 and 17 become more flexible with an increasing distance to the web 13. A design of the prongs 16 and 17, with which a change of the flexibility of the prongs 16 and 17 is achieved by way of using materials with a different flexibility for the individual sections of the prongs 16 and 17, is also possible.

The prongs 16 and 17 represented in the drawings comprise a first end portion 18, a second end portion 19 and a middle part 43, which extends between these end portions 18 and 19. The first end portion of the elongate prong base 18 is connected onto the web 13 and it is usefully designed as one piece with this. The second end portion 19 of the prongs 16 and 17 is designed as a thickened continuation and is located medially of the tendon plate of the Musculus gluteus medius and medially of the tip of the trochanter major fragment 9.

Figure 3:
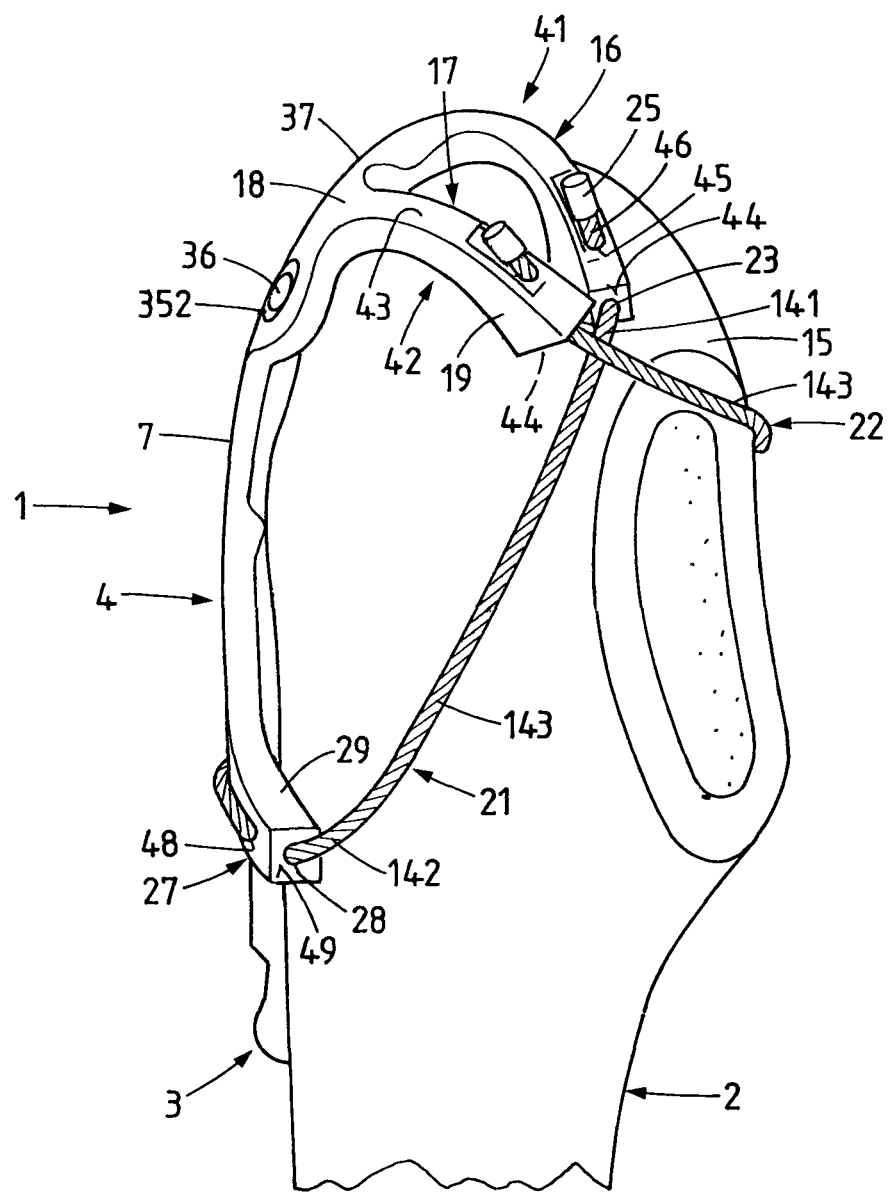
FIG. 3 the implant of FIGS. 1 and 2, in a dorso-medio-cranial view.

The width of the thickened continuation 19 is practically equal to the width of the prong 16 and 17. The height of the thickened continuation 19 on the other hand represents a multiple of the thickness of the middle portion 43 of the prong 16 and 17. The continuation 19 comprises an end-face 44 (FIGS. 2 and 3). A bore 23 runs through the thickening 19. One of the run-outs of this bore 23 lies in the end-face 44 of the thickening 19. The bore 23 runs obliquely upwards through the thickening 19, so that a second run-out 45 of the bore 23 lies in the surface of the thickening 19 or of the prong 16 and 17.

Figure 1:
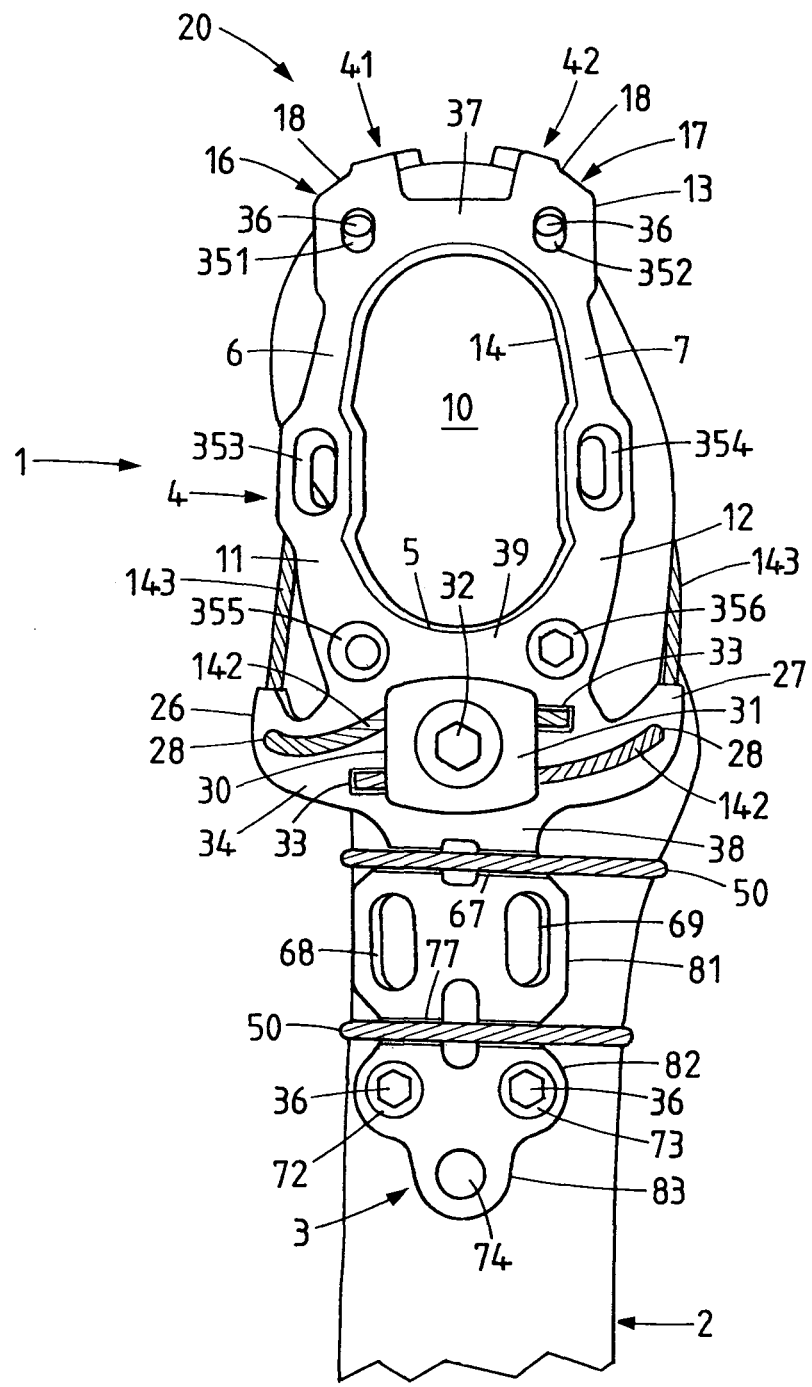
FIG. 1 a front view of the trochanter retention plate, which comprises a base plate and which is attached on the proximal femur of a left hip, wherein the base plate comprises a lower section.

The respective retainer 41 and 42 further comprises a flexible elongate member 21 and 22 respectively, which usefully has a circular cross section. The diameter of the longitudinal member 21 and 22 is smaller than the width of the prong 16 and 17 respectively. In the represented case, these elongate members 21 and 22 are designed as cables. These cables 21 and 22 may be cords or cables and they may be of stainless steel, titanium or plastic. The first end portion 141 of such an elongate member or cable 21 and 22 is connected to the second free end portion 19 of the corresponding prong 16 and 17 respectively (FIGS. 1 and 3).

The second or free end portion 142 of the longitudinal member or cable 21 and 22, after the cables 21 and 22 have crossed, is fastened to the base plate 1. The first end portion 141 of the cable 21 and 22 goes through the bore 23 in the thickening 19 of the prong 16 and 17 respectively, wherein an end section 46 of this first end portion 141 projects out of the upper run-out 45 of the bore 23 in the prong 16 and 17 respectively. This end section 46 projecting backwards from the bore run-out 45 is provided with a cap 25, which is attached on this cable end section 46. The cap 25 prevents this cable end section 46 from going through the bore 23 in the thickening 19 of the prong 16 and 17. A recess may be designed in the upper side of the thickening 19 in the region of the upper run-out 45, in which recess the cap 25 has space. This recess in the prong end portion 19 may be designed so deep, that the upper contour of the cap 25 lies below the surface of this prong end portion 19. Other options of the connection between this prong end 19 and the end 141 of the cable 21 and 22 are firm press connections or movable eyelets, joint designs etc. After the exit from the end-face 44 of the prongs 16 and 17, the cables 21 and 22 cross over the fossa trochanterica 15. The result of this is the fact that that end 21 which is connected to the ventrally lying prong 16, runs dorsally and distally with respect to the fossa trochanterica 15. That cable 22 which is connected to the dorsally lying prong 17, runs ventrally and distally with respect to the fossa trochanterica 15. The cables which are crossed over the fossa trochanterica block with one another amid tension at the free ends 19 of the prongs 16 and 17. After the crossover, the cables 21 and 22 are led to the base plate 1, where their second or free end portions 142 are held by a clamping device 30.

The clamping device 30 is arranged on the outer side of the base plate 1 and is arranged practically between the lower section 3 and the upper section 4 of the base plate 1. The clamping device 30 (FIGS. 1 and 2) comprises a clamping plate 31, and in the shown case, a screw 32, advantageously a fine-thread screw. It is particularly advantageous if the threaded bolt of this fine-thread screw 32 has an as large as possible diameter. The base plate 1 in this region of this has a threaded bore (not shown), in which the threaded bolt of the screw 32 may be screwed. The two end portions 142 of the cables 21 and 22 lie between the base plate 1 and the clamping plate 31. Thereby, the second end portion 142 of the first cable 21 lies below the screw bolt of the screw 32, and the second end portion 142 of the second cable 22 lies above the screw bolt of the screw 32. In order to keep the height of this region of the implant as low as possible, recesses 33 are designed in the base plate 1 and/or the clamping plate 31, where the two end portions 142 of the cables 21 and 22 are located. These recesses 33 accommodate the end portions 142 of the cables 21 and 22.

It has generally been found to be advantageous, in each case to incorporate an elongate recess above and below the threaded hole in the outer side of the plate main part, for receiving the respective free end portion of the cables. These recesses extend preferably almost perpendicularly to the longitudinal direction of the plate limbs, and are designed with only such a depth, that the cable applied into the respective recess may be clamped between the base of this recess and the clamping plate, when the screw is tightened.

As will yet be described hereinafter, according to further preferred embodiment examples, the retainers, or the longitudinal members, do not engage at the free end portions of the respective prongs, but at a position which is set back in the direction of the prong base. In preferred embodiments, they engage on the prong base itself, are led along the prongs, and pass through the thickening which is arranged at the respective free end portion of the prongs. If one pulls at the free end of a longitudinal member, then the respective prong is bent under the influence of the longitudinal member, wherein the longitudinal member introduces the force into the prong uniformly over the length.

Elongate extensions 26 and 27 for guiding the second end portions 142 of the cables 21 and 22, which lie here, are provided (FIG. 1 to 3), so that the cables 21 and 22 are not buckled by way of fastening in the clamping device 30. The first extension 26 is directed in a medial manner ventrally on the trochanter massif (calcar femoris), and the second extension 27 is directed in medial manner dorsally on the trochanter massif (calcar femoris). These guide extensions 26 and 27 are arranged in front of the clamping device 30. The respective guide extension 26 or 27 projects from one of the side edges of the upper section 4 of the base plate 1. The respective guide extension 26 or 27 connects to the main part 5 of the base plate 1, between the upper horizontally running edge portion 39 of this main part 5, and the lower horizontally running edge portion 38 of this.

The elongate base body of the respective guide extension 26 or 27 is bent in two directions. The first bending of the elongate guide extension 26 or 27 lies roughly in a horizontal plane, and the course of this corresponds roughly to the course of the bending of the surface of the bone 2, to which the extensions 26 and 27 are assigned. The second bending of the elongate guide extension 26 and 27 lies roughly in a vertical plane. The respective guide extension 26 and 27 is bent upwards in this vertical plane, and specifically corresponding to the course of the second end portions 142 of the crossing cables 21 and 22, which in this region of the base plate 1 are held by the clamping device 30.

The exposed end portion 29 of the bent guide extension 26 and 27, in the represented case, is thicker than that end portion 34 of the guide extension 26 and 27, which is connected to the main part 5 of the base plate 1. The exposed end portion 29 of the extension 26 and 27 comprises a bore 28. This bore 28 runs from the end-face 49 of the exposed end portion 29 of the guide extension 26 and 27, towards the base plate 1, and specifically obliquely upwards, so that the second run-out 48 of this bore 28 lies in the outer surface of the bent guide extension 26 and 27. The bore 28 in the ventral extension 26 is provided for leading through the cable 22, which is led up from the dorsal prong 17. The bore 28 in the dorsal extension 27 is envisaged for leading through the cable 21, which is led from the ventral prong 16.

It is particularly the case with embodiments of the implants according to the invention, which are applied with ETO, that it has been found to be advantageous, as will yet be explained in more detail hereinafter, to cross the flexible, elongate members over the fossa trochanterica 15 directly after leaving the prong, to lead them from there to the medial periphery of the trochanter massif (calcar femoris) and to cross them there once again and then to lead them approximately perpendicularly to the longitudinal axis of the shank, back again to the clamping device of the base plate. One may therefore make do without the guide extensions 26 and 27, as is indicated with the base plates of the FIGS. 14, 17 and 18.

The lower section 3 of the base plate 1 connects to the lower edge 38 of the main part 5 of the upper plate section 4, and specifically below the clamping device 30. The lower section 3 of the base plate 1 is of one piece with the upper plate section 4.

The lower section 3 of the base plate 1, similarly to the upper section 4 of the base plate 1, comprises a surfaced base body or main part which is designed arched in an elongate manner. The longitudinal axis of this elongate curvature coincides with the longitudinal axis of the curvature of the outer surface of the femur 2 or it runs at least parallel thereto. The curvature of this lower section 3 of the base plate 1 should correspond to the curvature of the surface of that section of the femur 2, to which this section 3 of the base plate 1 is to be assigned. It is to be understood that the curvature of this section 3 of the base plate 1 may change along its practically vertically running longitudinal axis, depending on how the horizontally running curvature of the surface of this section of the femur 2 changes in its longitudinal direction.

A first main task of the lower section 3 of the base plate 1 lies in neutralising the abductor forces coming laterally from the prong and medially from the cable ends. A second main task of the lower section 3 of the base plate 1 is to ensure the rotation stability of the design in the case that the vector of the abductor tension is no longer identical with the longitudinal axis of the femur 2.

The distal section 3 of the base plate 1 comprises three regions 81, 82, and 83 (FIG. 1). The upper region 81 of the distal section 3 of the base plate 1 connects to the lower edge 38 of the proximal region 4 of the base plate 1. A first groove 67 is designed between these in the outer side of the distal section 3 of the base plate 1, and runs practically perpendicular to the longitudinal axis of this distal section 3 of the base plate 1. Two elongate holes 68 and 69 which are located at a distance to one another, are designed in this upper region 81 of the distal section 3 of the base plate 1. The longitudinal axis of these elongate holes 68 and 69 runs vertically. A second groove 77 is designed in the outer side of the distal section 3 of the base plate 1, between the upper region 81 and the middle region 82 of the distal section 3 of the base plate 1. Likewise, two holes 72 and 73 are designed in the middle region 82 of the distal section 3 of the base plate 1, which however may have a circular contour. In each case, one of these circular holes 72 and 73 lies below one of the elongate holes 68 and 69 respectively, in the upper region 81. A hole 74 is formed centrally in the lower region 83 of the distal section 3 of the base plate 1. The fixation of the distal section 3 of the base plate 1 on the proximal, lateral femur 2 may be effected by way of screw elements, which go through the holes 68 and 69 in the upper region 81 of the distal section 3 of the base plate 1 and/or through the holes 72 and 73 in the middle region 82 of the distal section 3 of the base plate 1.

Figure 4:
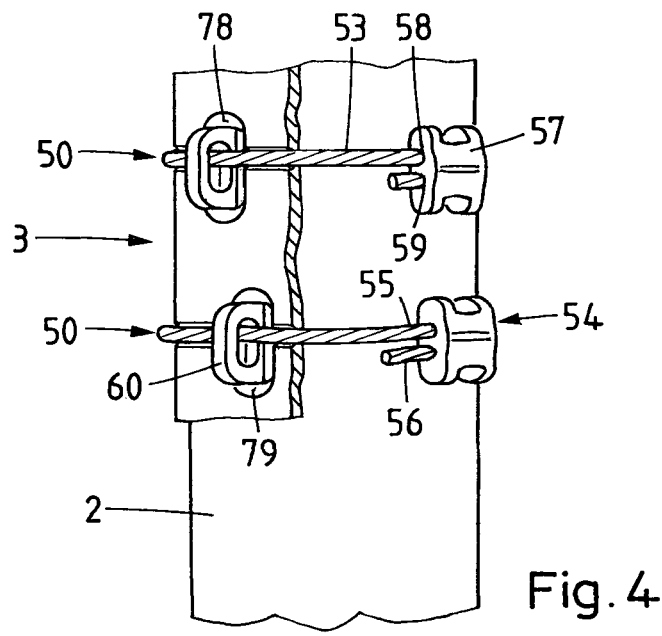
FIG. 4 a simplified cut-out of the lower section of the base plate of FIG. 1, which is fixed on the bone by way of fixation devices.

FIG. 4 shows a cut-out of the lower section 3 of the base plate 1, which is fastened on the bone 2 with the help of fixation devices or cable cerclages 50. The fixation device 50 comprises an elongate and flexible member 53 (FIGS. 1 and 4), which is applied around the femur in an annular manner. This member 53 is usefully a cable. The cable 53 lies in one of the grooves 67 or 77 in the lower section 3 of the base plate 1, and its remaining part surrounds the femur 2. The cable 53 has end portions 55 and 56. The fixation device 50 further comprises a clamping means 54 which may hold together the end portions 55 and 56 of the cable 53 applied around the femur 2. The clamping means 54 have a base body 57 of a material, which despite being shape-stable, may be deformed amid the application of a significant mechanical force, for example exerted by pliers. Two continuous bores 58 and 59 are formed in the base body 57 of the clamping means 54, and extend in the longitudinal direction of the clamping means 54. These bores 58 and 59 lie next to one another and they run practically next to one another. The diameter of these bores 58 and 59 is selected such that one of the cable ends 55 and 56 may pass through one of the bores 58 and 59 respectively, in a straight manner. After the base body 57 of the clamping means 54, as mentioned, has been deformed, in particular pressed together, the shape of the cross section of the holes 58 and 59 is also changed, in particular pressed together. By way of this, the cable ends 55 and 56 are firmly clamped in these bores 58 and 59 and are firmly held by the clamping means 54.

The distal section 3 of the base plate 1 may be fixed on the femur 2 in a temporary manner by way of the primary occupation of the elongate holes 68 and 69 and/or 72 and 73 with screws. The occupation of the holes 72 and 73 in the middle region 82 of the distal section 3 of the base plate 1 is effected selectively with tension screws or angularly stable screws. The opening 74 lying centrally and distally in the lower region 83 of the distal section 3 of the base plate 1 serves for the application of a plate approximator for the digitalisation of the complete tension band design. Subsequently, one or two fixation devices 50 are attached, wherein the cable 53 of the respective fixation device 50 comes to lie in one of the grooves 67 or 77.

The base body of the lower section 3 of the base plate 1 is relatively thin, so that the grooves 67 and 77 may not be too deep in this. This may lead to the cable 53 leaving the groove 67 and 77 under certain circumstances, which may result in the fixation device 50 displacing in the longitudinal direction of the bone 2. In order to prevent this, the base body of the lower section 3 of the base plate 1 comprises elongate holes 78 and 79 lying above one another, whose longitudinal axis runs in a practically vertical manner. A holder 60 is provided, which is envisaged and designed for positioning the cable 53 in the longitudinal direction of the lower section 3 of the base plate 1 on the femur 2.

Figures 5, 6:
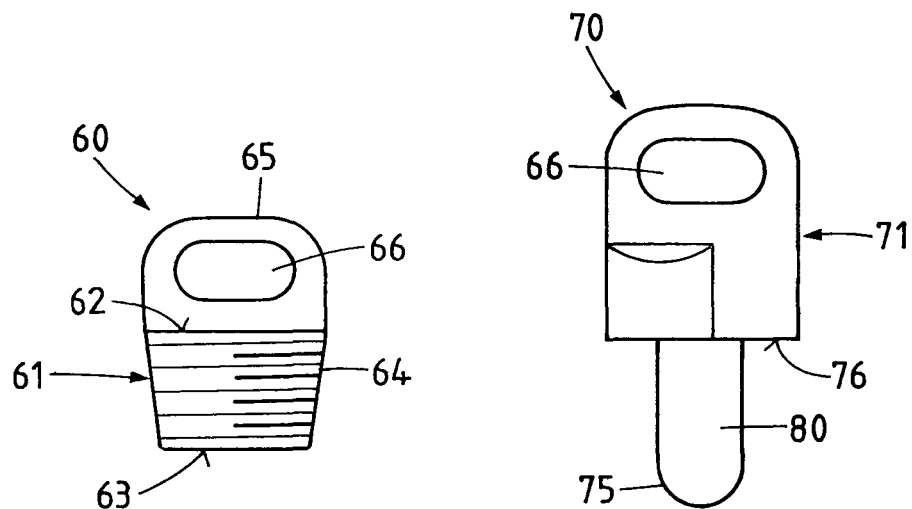
FIG. 5 a first embodiment of the fixation device of FIG. 4, in a lateral view.
FIG. 6 a second embodiment of the fixation device, in a lateral view.

FIG. 5 in a lateral view, shows a first embodiment of such a holder 60 of the fixation device 50. This holder 60 comprises a base body 61 which is envisaged and designed for inserting into one of the elongate holes 78 and 79 in the lower section 3 of the base plate 1. The holder base body 61 is roughly conical, wherein this cone 61 has an upper end-face 62 and a lower end-face 63. The lower end-face 63 has a smaller diameter than the upper end-face 62. The distance between the end-faces 62 and 63 may be equal to the thickness of the lower section 3 of the base plate 1, or it may be somewhat larger than this. The surface 64 of the cone 61 is provided with a thread or at least with projections. An eyelet 65 projects from the larger end-face 62 of the cone 61 and is of one piece with the base body 61 of the ring holder 60. An opening 66 through which the section of the cable 53 which extends between the end portions of this cable passes, is formed in the eyelet 65. Usefully, the opening 66 is designed as an elongate hole, wherein the longitudinal axis of this elongate hole 66 in the ring holder 60 runs roughly parallel to the upper end-face 62 of the ring holder 60. Firstly, the cable 53 is led through the opening 66 on the eyelet 65 of the ring holder 60. Then, the ring holder 60 is inserted into one of the openings 78 and 79 in the lower section 3 of the base plate 1. Thereafter, the cable 53 is applied around the bone 2, and the cable ends 55 and 56 are inserted through the bores 58 and 59 in the clamping means 54. The base body of this clamping means 54 is deformed amid the tension of the cable ends 55 and 56, in particular pressed together. What is advantageous with this design of the ring guide 60, is the fact that the ring guide 60 sits firmly in the lower section 3 of the base plate, and that it therefore does not touch the bone 2 or only to a minimal extent. Under certain circumstances however, a second embodiment of the ring holder 70 is useful, which is represented in FIG. 6 in a lateral view. This ring holder 70 comprises an essentially surfaced base body 71, whose cross section may be oval. As a result, this base body 71 may go through one of the oval openings 78 and 79 in the lower section 3 of the base plate 1. In the upper region of the ring guide 70, the already described opening 66 for leading through the cable 53 is present. A peg 80 projects from the lower end-face 76 of the base body of the ring holder 70. The free end portion 75 of this peg 80 is rounded. In order for this ring guide 70 to be able to be inserted, a recess (not shown) must firstly be drilled in the bone 2, into which the peg 80 comes to lie, after this ring holder 70 has been inserted into one of the elongate holes 78 and 79.

The described base plate 1, which is fixed on the proximal femur 2, the prongs 16 and 17, as well as the cables 21 and 22, form a tension band design which encompasses the trochanter fragment 9 laterally as well as cranially and medially, so that this is held at an anatomical position.

The osteotomised/fractured trochanter major 9 is fixed manually or with a clamp, and is circumscribed from the dorsal-medial with a tubular cable adapter (not shown). Thereby, the tendon plate coming from the medial-dorsal, is pierced directly above the tip of the trochanter fragment 9 in the ventral half. The cable 21 of the ventral prong 16 is led through the thus presented cable adapter, so that the cable 21 runs from the ventral over the trochanter tip and pulls to the dorsal-medial. From there, the cable 21 is led back further on the dorsal side along the proximal femur 2, to the base plate 1. Subsequently, the second cable 22 is accordingly led from the dorsal over the trochanter tip to the ventral-medial and then further ventrally on the proximal femur 8 to the base plate 1. Amid pulling at the two free cable ends 142 and simultaneously slight pressure on the proximal region 4 of the base plate 1 to the medial, the prongs 16 and 17 are pushed through the tendon plate of the musculus gluteus medius until the pre-bent curvature of the prongs 16 and 17 encompasses the trochanter tip. By way of simultaneously pulling at the free ends 142 of the two cables 21 and 22 and by way of simultaneously exerted pressure on the base plate 1, the reposition of the trochanter fragment 9 may now be carried out for the sake of a test. With this reposition, the leg should advantageously be held in abduction and outer rotation. By way of this, the tension of the Musculus gluteus medius is reduced, and the reposition is simplified. With an anatomical reposition, the base plate 1 should lie distally of the tuberculum innominatum 10, and the ventral plate limb 6 should lie ventrally, and the dorsal plate limb 7 dorsally, of the tuberculum innominatum 10. If the plate 1 is not correctly positioned in height, in particular is too high, i.e. lies on the tuberculum innominatum 10, then the prongs 16 and 17 should be bent afterwards, so that the optimal position is achieved. With a correct plate position, the two elongate holes 68 and 69 in the distal region 3 of the base plate 1 may now be provided with screws (not shown) at the distal hole end. Subsequently, the free ends 142 of the cable 21 and 22 are led through the guide extensions 26 and 27 respectively of the base plate 1, up to the clamping device 30 and below the clamping plate 31. Thereby, the ends 142 of the cables 21 and 22 are applied below the clamping plate 31, such that with a later tightening of the fine thread screw 32 of the clamping device 30 (right-hand thread), the cables 21 and 22 have a tendency to be additionally tensioned.

Now the cables 21 and 22 are tensioned with a double-sided cable tensioner (not represented). Thereby, the end portions 19 of the flexible plate prongs 16 and 17 block at the crossing of the cables 21 and 22, i.e. above the fossa trochanterica 15. With a further tension, the flexible prongs 16 and 17 of the base plate 1 adapt to the contour of the cranial circumference of the trochanter major 9, and tighten this at an anatomic position. The cables 21 and 22 are tensioned to such an extent, that an adequately high tension is achieved, without deforming the trochanter major 9 or luxating it out of its bone-setting position.

Figure 16:
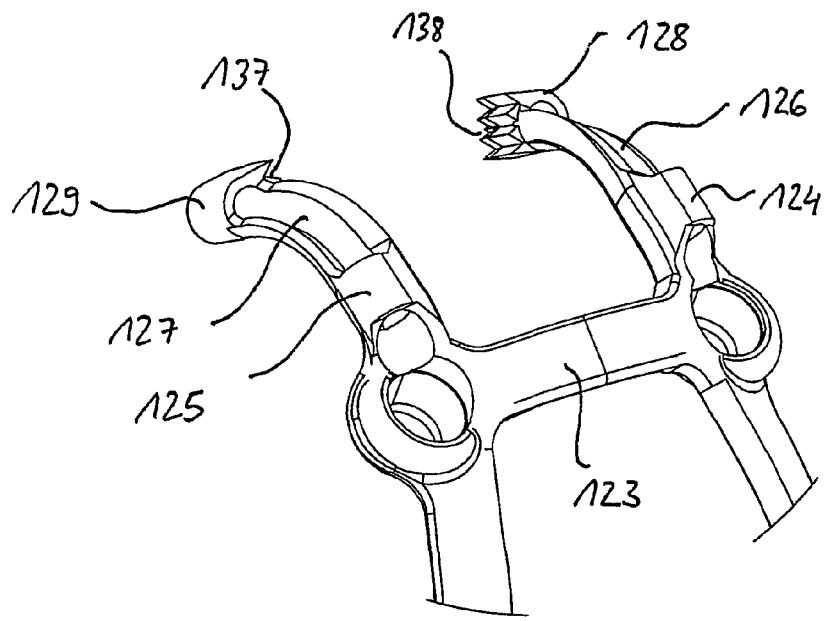
FIG. 16 a detailed enlargement D of the proximal end region of the implant according to FIG. 14a, in the view according to FIG. 14f.

One preferred design of the end portions or the thickenings 128, 129 of the flexible plate prongs is represented in FIG. 16, and this design supports the blocking of the prongs by way of a positive-fit engagement of corresponding toothed inner surfaces 137, 138.

According to preferred embodiments, several options exist for the further steps:

Option 1: Leaving the double-sided cable tensioner, occupying at least two options of the holes 68 and 69 in the distal region 3 of the base plate 1 of the two holes 72 and 73 in the middle part 82 of the distal region 3 of the base plate 1, with screws 36. The screw holes 355 and 356 are to be obligatorily occupied with screws 36. Of the four possible angularly stable screws 36 in the proximal, flexible section 4 of the base plate 1, at least two are to be occupied. Subsequently to this, the cable tensioner should once again be retightened, and thus the definitive tension of the cables 21 and 22 created. At the close, the fine thread screw 32 of the clamping device is tightened, and the protruding cable ends 142 are cut away.

Option 2: Fixing of the cables 21 and 22 by way of tightening the fine-thread screw 32 of the clamping device 30, and the slight opening of the screws 36 in the elongate holes 68 and 69. Installing an approximator at the distal hole 74 of the base plate 1, by which means the complete plate-cable design is distalised and an even higher pressing pressure above the trochanter osteotomy/trochanter fracture is produced. Tightening the screws in the elongate holes 68 and 69 and occupation of the screw holes 72 and 73, as is described in option 1. The screw holes 355 and 366 must be occupied. Finally, the cables ends 142 are cut away.

Option 3: The fixation of the base plate 1 on the proximal femur 2 may be effected exclusively or in combination with cables 21 and 22, via the grooves or recesses 67 and 77 in the distal section 3 of the base plate 1, which are provided for this. This variant is applied if damage to the prosthesis shank due to a possible drilling on introducing the screws 36, is to be avoided at all costs. The fixation is then effected as in option 2, not by the provision of the screws 36, but usually by way of the application of fixation devices 50. The screw holes 355 and 356 must be occupied.

Option 4: The cables 21 and 22, after exit from the prongs 16 and 17 and the crossing at the fossa trochanterica 15, may additionally be led around the proximal femur 8 below the trochanter minor medial, and then led back to the base plate and fixed there. By way of this, the tension vector of the cables 21 and 22 is directed to the caudal-medial and thus a possible luxation of the tension band design laterally over the osteotomy plane OF is prevented. The screw holes 355 and 356 must be occupied.

According to a further advantageous embodiment of the above mentioned invention, the implants for the refixation of the osteotomised or fractured trochanter major comprise at least one plate which may be fixed on the proximal femur and which is held on the femur with a non-positive fit. The plate comprises at least one proximal extension which is connected with at least one retainer to an opposite side of the trochanter major, said retainer running back to the plate, being fixed there as described above and forming a "closed system" with the at least one proximal extension. The at least one proximal extension and the at least one retainer, together form a tension band design which runs over the trochanter major 9.

In particular, the lower section of the base plate, hereinafter also called plate shank or shank for short, undergoes modifications in preferred embodiments, as are described briefly hereinafter The length of the shank may be varied, wherein the maximal length is a femur length. Implants according to the invention with a short shank are particularly suitable for traditional osteotomies of the trochanter major, with which only the tip of the trochanter major is obliquely recessed. A medium shank length has shown its worth with total osteotomy, and implants with a long shank are in particular suitable with so-called extended osteotomy. The long shank versions may be applied with all types of osteotomy, wherein although being operatively technically possible for traditional and total osteotomy, they are often just not necessary.

In particular with total osteotomy, in order to prevent the implant from building up and becoming a hindrance, the shank may be almost completely reduced, so that the base plate is fixed on the femur for example only by way of two screws.

Figure 7:
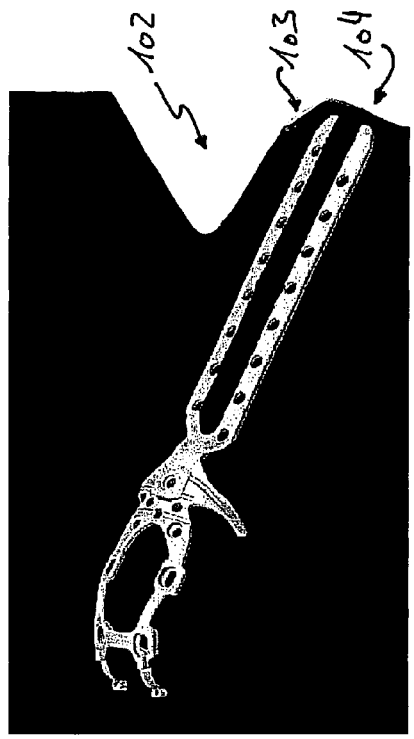
FIG. 7 a further embodiment of the implant according to the invention, with which the lower section of the base plate is designed as a long, narrow plate shank.

A further embodiment of an implant according to the invention is represented in FIG. 7, with which the lower section of a base plate 100 is designed as a long, narrow plate shank 101, which as will yet be described hereinafter, is very suitable for sliding under the M. vastus lateralis on implantation. According to an advantageous embodiment, which is not shown in the figures, the shank is designed in a wave-like manner, so that with regard to its construction, it corresponds to a snake plate, as is known from the company Icotec. With regard to the wave-like shank, the receiver openings for the screws are not arranged in a line, so that no break-line is generated.

Figure 8:
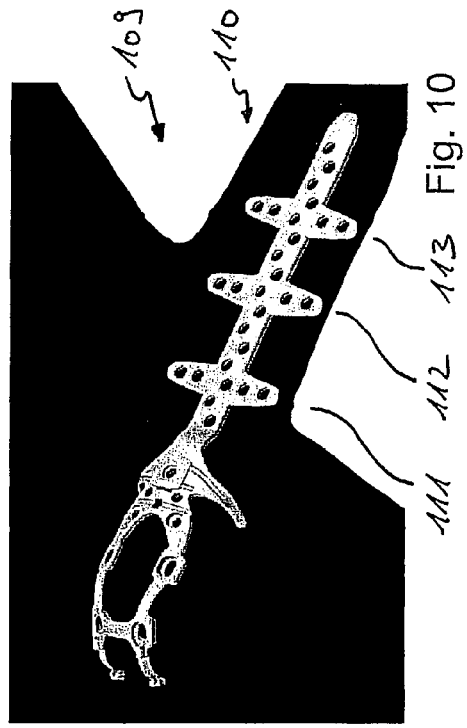
FIG. 8 a further embodiment of the implant according to the invention, with which the lower section of the base plate is designed as a forked plate shank with two longitudinal wings, which are distanced to one another.

A further advantageous embodiment is shown in FIG. 8, with which the lower section of the base plate is designed as a forked plate shank 102 with two longitudinal wings 103, 104 which are essentially parallel and distanced to one another. The longitudinal wings 103, 104 engage below the clamping device at the distal end of the upper section. In the present embodiment, each individual wing may be designed more narrowly than the shank with single-wing variants (such as according to FIG. 7 for example), without compromising the stability. The narrow longitudinal wings have the advantage that they may be sled even more easily below the M. vastus lateralis with the operation. The origin of the M. vastus lateralis accordingly does not need to be detached or only slightly on implantation, if the implant with the two-winged plate 102 is introduced from the proximal. The wings 103, 104 in further, non-represented embodiments, may be connected to one another in a rigid or articulated manner.

Figure 9:
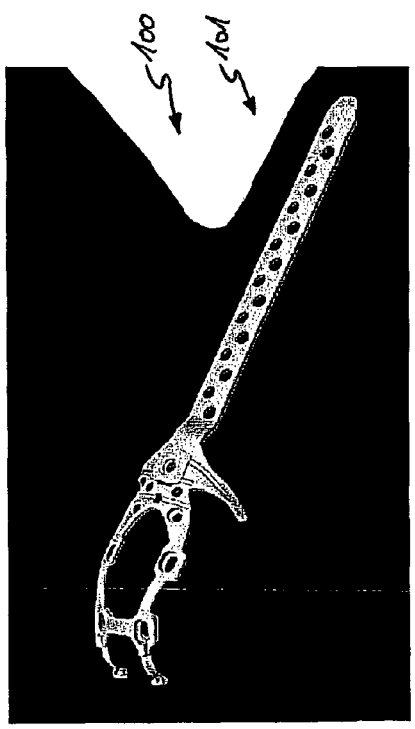
FIG. 9 a further embodiment of the implant according to the invention, with which the lower section of the base plate is designed as a long, wide plate shank, FIG. 10 a further embodiment of the implant according to the invention, with which the base plate is designed as a long, narrow plate shank with six lateral wings projecting perpendicularly.

A further advantageous embodiment of the base plate of the implant according to the invention is represented in FIG. 9. The lower section of the base plate is hereby designed as a wide shank 105, which permits an even better fixation on the bone. The wide fixation improves the resistance with respect to the lever effect with rotation movements, in comparison to a narrow plate. A further advantage of the wide shank occurs with the application in so-called extended trochanteric osteotomy (ETO). The shank 105 comprise three segments 106, 107, 108, wherein components of the dorsal and ventral segments 106 and 108 project beyond the osteotomy line of the extended trochanteric osteotomy, so that the shank 105 may be fixed on the other side (region b) and on this side (region a), of the osteotomy line, preferably by way of screws. The plate-like shank 105 is fixed with screws on both sides of the osteotomy line, which means that it is fixed on the distal fragment of the femur and in the osteotomy fragment/trochanter fragment and with this prevents the proximal movement of the osteotomy fragment/trochanter fragment.

Figure 10:
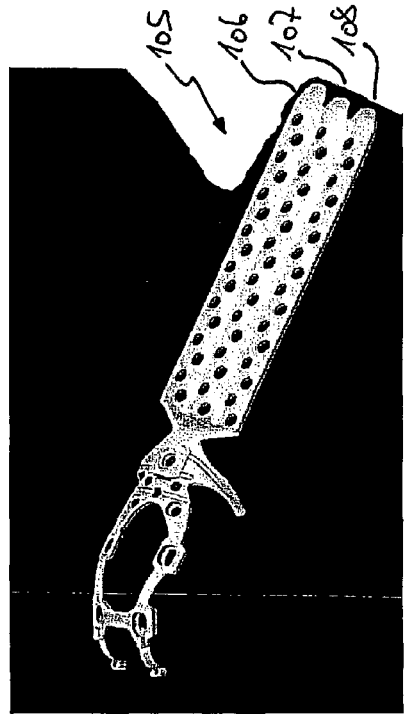

A similar advantageous effect with extended trochanteric osteotomy may be achieved with an implant with a base plate 109 according to a further embodiment, as is shown in FIG. 10. The base plate 109 is designed as a long, narrow plate shank 110, from which three pairs of lateral wings 111, 112, 113 project in an essentially perpendicular manner. It is evident to the man skilled in the art, that the lateral wings 111, 112, 113, which in the picture are represented approximately in a plane with the shank 110, are adapted intraoperatively to the geometry of the femur, and are deflected out of this common plane after the fixation. The shank 110 provided with lateral wings 111, 112, 113 again is fixed with screws on both sides of the osteotomy line in the distal fragment of the femur as well as in the osteotomy fragment/trochanter fragment, and very effectively prevents the proximal movement of the osteotomy fragment/trochanter fragment.

Figure 11:
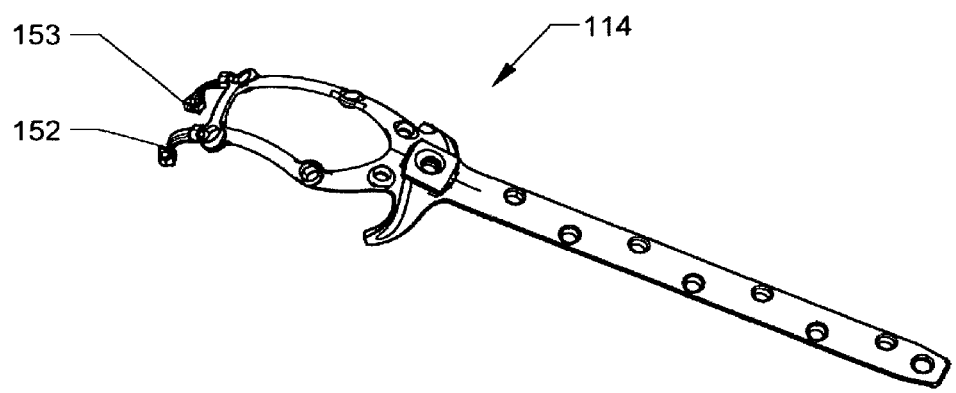
FIG. 11 a further embodiment of the implant according to the invention, with which a transverse web of the upper section of the base plate is not formed.
Figure 12A:
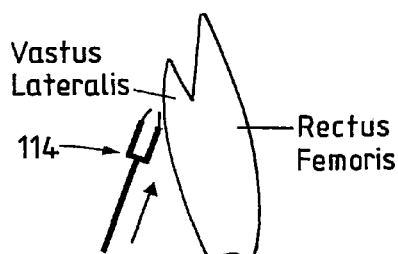
FIGS. 12a to 12c schematic representations of the introduction of an implant according to 1, distally of the origin of the M. vastus lateralis.
Figure 12B:
Figure 12C:

A base plate 114 of an implant according to the invention is represented in a further embodiment in FIG. 11, with which the upper section of the base plate is designed without a transverse web. By way of this, the base plate 14, as sketched in FIGS. 12*a* to 12*c*, may be led around, with the upper two plate prongs 115, 116, from the distal of the origin of the M. vastus lateralis, anterior and posterior of the muscle original, without this having to be separated away, in particular with minimal invasive implantation (above all with complete osteotomy). The base plate 114 on the part of the manufacturer may already be manufactured without a transverse web, or a plate with a transverse web design is provided with suitable grooves or similar break-off locations, so that the transverse web may be intraoperatively removed by the operator when required.

Figure 13A:
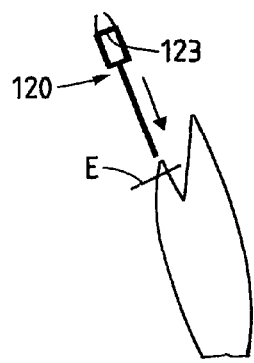
FIG. 13a to 13c schematic representations of the introduction of an implant according to FIG. 7, from the proximal, after cutting into a short portion of the origin of the M. vastus lateralis.
Figure 13B:
Figure 13C:
Figures 14A, 14B, 14C, 14D:
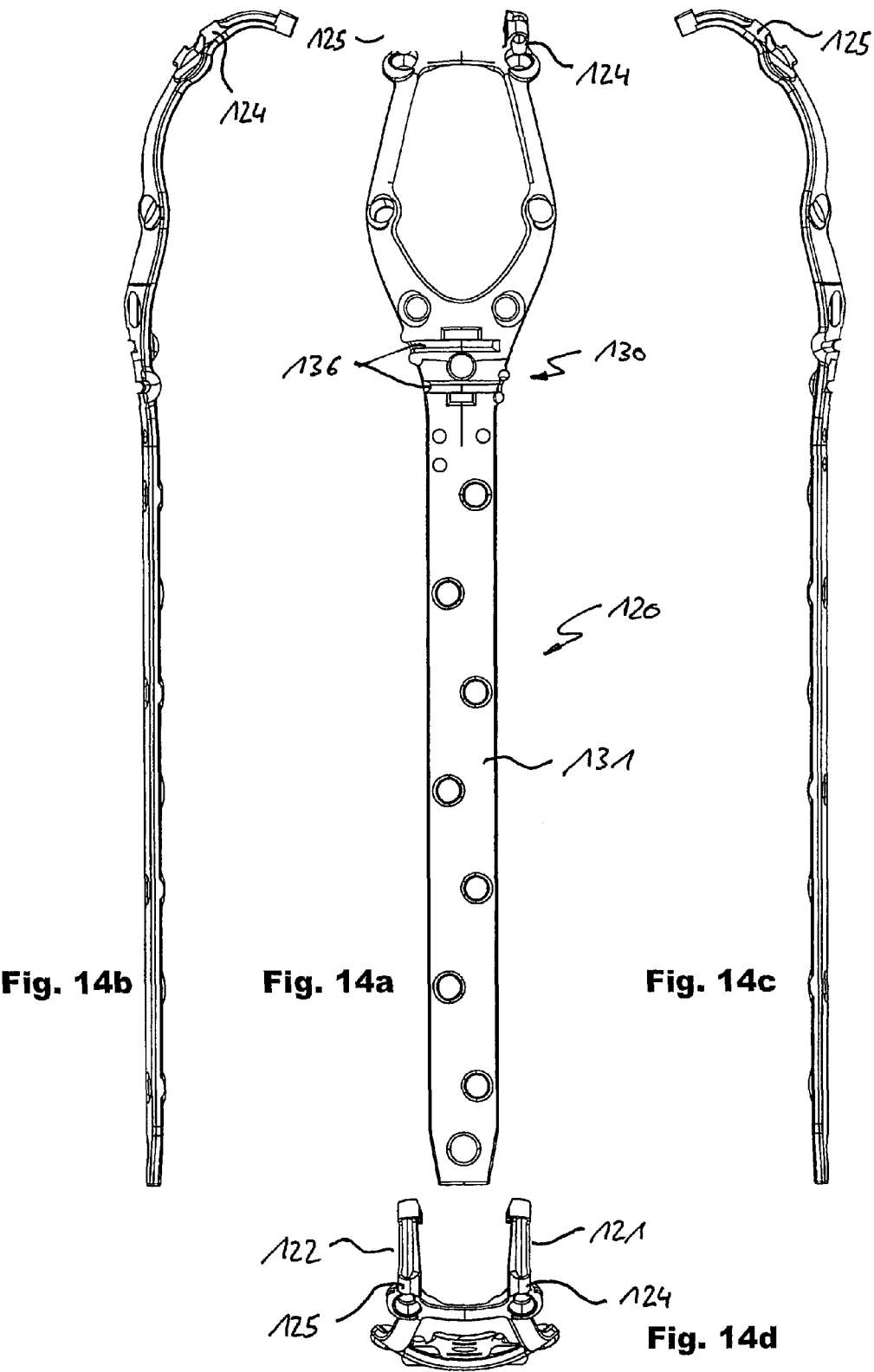
FIG. 14a a further embodiment of the implant according to the invention, with which guide run-outs arranged in front of the clamping device are not formed.
FIG. 14b to 14d the implant according to FIG. 14a, in views from the ventral, dorsal and proximal.
Figure 14F:
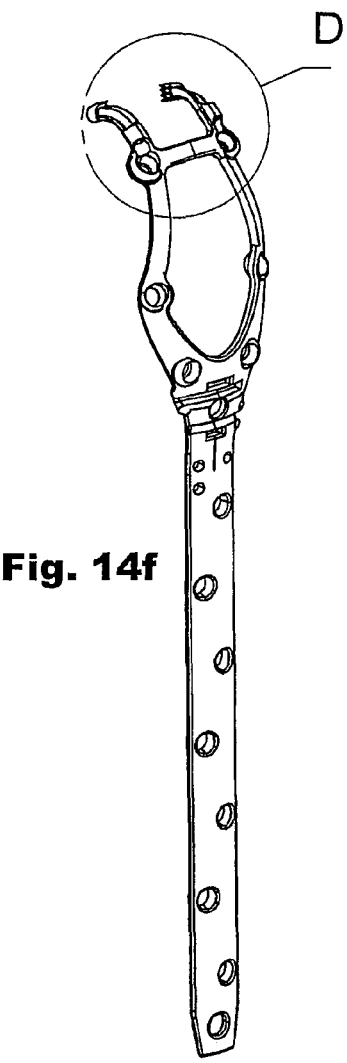
FIG. 14e and 14f the implant according to FIG. 14a in perspective views from the dorso-medial and ventro-lateral.
Figure 14E:
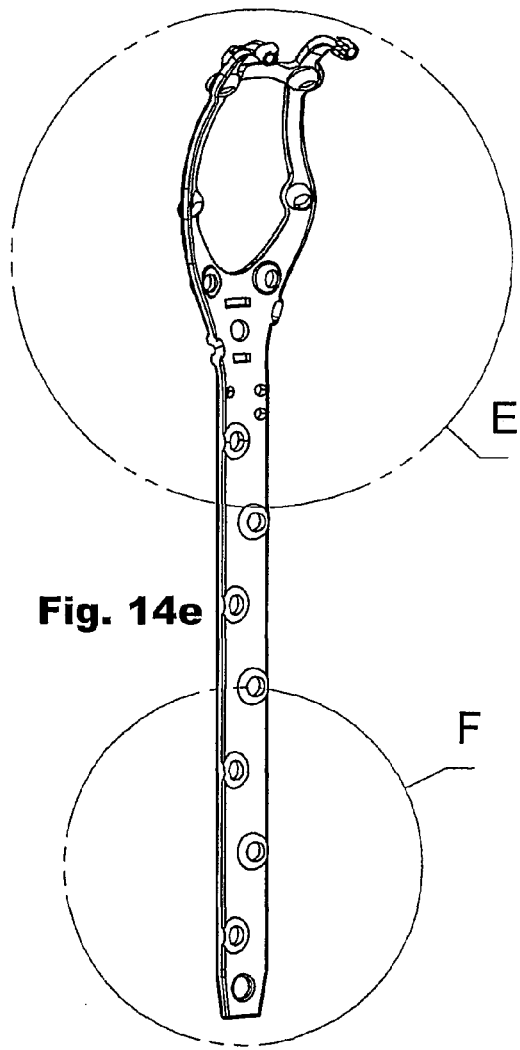

One example of the operative application of a base plate 120 with a transverse web 123 at the upper section, as is shown for example in FIG. 14, is represented in the FIGS. 13*a* to 13*c*. The base plate 123 with a transverse web is inserted from above/proximal below the origin of the M. vastus lateralis (indicated in FIG. 13*a* by a short black transverse dash E) after cutting into a small part of this M. vastus lateralis.

Hereinafter, further advantageous features of the present invention are dealt with by way of the base plate 120, as is represented in the FIGS. 14 to 19, and these features, inasmuch as not expressly mentioned, may also be realised with other embodiments of the implants according to the invention.

One may easily recognise from the various views of FIG. 14 and in particular from the detail enlargement D as is represented in FIG. 16, that the end sections of the retainers may not only engage on the first end portion, which means at the tip, of the prongs 121, 122, but also at the oppositely lying end portion, thus the prong base. For this, in each case a thickening 123, 124 is arranged on the base of the prongs 121, 122, and this thickening is provided with a bore for leading through the flexible elongate members, as has already been described above for the thickenings on the tips of the prongs of the embodiment according to FIGS. 1 to 3. The members, preferably cables, which are not drawn in the FIGS. 14 to 18, are again provided with caps preferably at their rearwardly projecting end sections, which prevent the respective cable section being able to be pulled through the bore in the thickening 124, 125. The prongs are provided with a guide groove 126, 127 at the upper side, which guides the cable along the prong 121, 122 to the longitudinal bore in the thickening 128, 129 at the prong tip, and secures it from dislocation under tensile loading.

The base plate 100 shown in FIG. 12, with a long shank 130, has been shown to be advantageous with extended trochanteric osteotomy (ETO), with which an alternative course of the retainers, preferably in the form of cables, is provided. The base plate 120 has no guide extensions for receiving the led-back cables. With the embodiments described above (according to FIG. 2) such guide extensions are arranged on the side edges of the main part 5 of the base plate 1, between the upper, horizontally running edge portion 39 of the main part 5 and the lower, horizontally running edge portion 38 of this, at the height of the clamping device 30. With regard to the base plate according to FIG. 14, one may make do without the guide extensions for receiving the led-back cables, which may be of a hindrance, in particular with minimal invasive implants, since the cables return to the base plate horizontally around the trochanter massif (Calcar femoris). The two cables, after leaving the prongs, run in a crossed manner over the fossa trochanterica and from there to the medial periphery of the trochanter massif (calcar femoris). There, the cables again cross and they go approximately perpendicular to the longitudinal axis of the shank, back to the clamping device 130 of the base plate 120. Thereby, with ETO, one effectively prevents the cables slipping into the osteotomy, and having no grip on the femur.

In the case of standard osteotomy or more difficult conditions for the leading of the cable medially along the femur (calcar femoris), the cables, after the first crossing over the fossa trochanterica, as with the previously described embodiments, may optionally be led back directly to the plate. With such cases, one may apply a clamping plate shown in FIG. 18, or compression plate 132 with lateral extensions 133, 134, for an improved guiding of the cables in the end region. A lead-through-opening 135 in the tip of the run-out 133, 134 in each case accommodates a cable and leads it to the actual clamping region in the centre of the compression plate. The clamping of the cables and the design of the grooves or recesses 136 for reducing the construction height of the implant in the region of the clamping device, thereby do not differ significantly from the previously described embodiments.

Figure 18A:
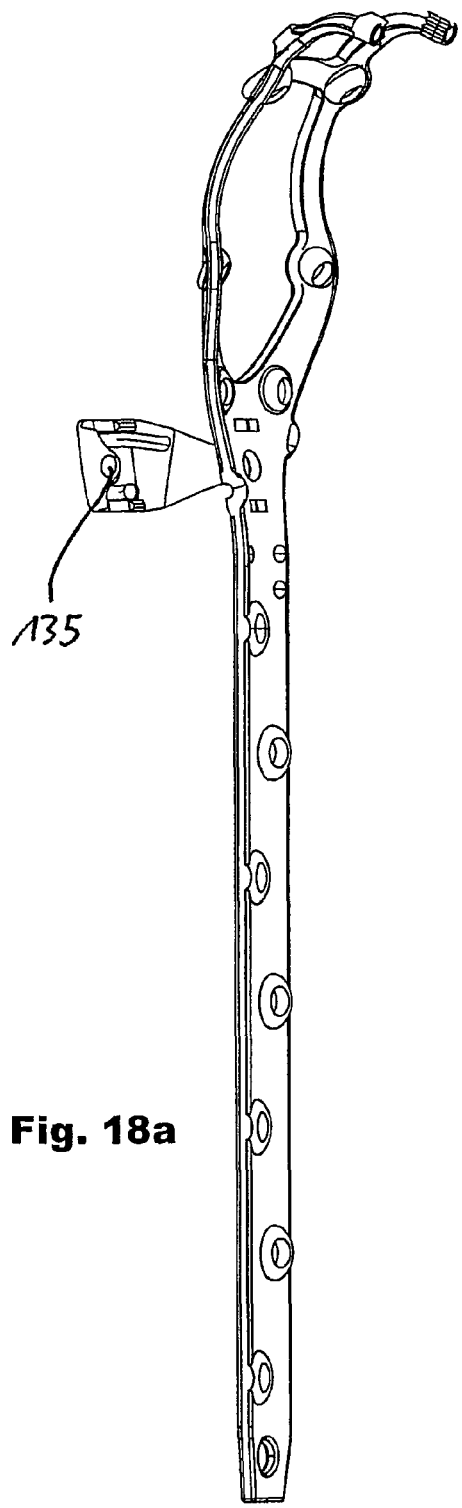
FIG. 18a and 18b the implant according to FIG. 14 together with a clamping plate according to a further embodiment of the invention, in perspective exploded views from the dorso-medial and the dorso-lateral.
Figure 18B:
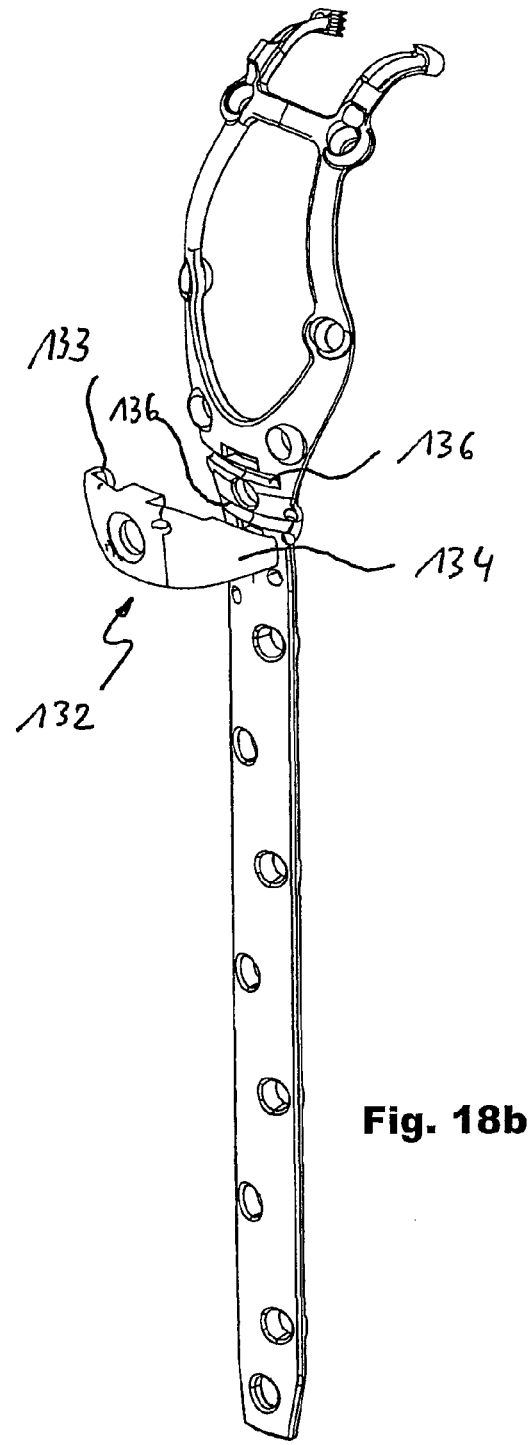

For standard osteotomy and complete osteotomy, in contrast to ETO, one advantageously uses an implant, with which the base plate corresponds to the base plate according to FIG. 18 with regard to all essential features, but the shank is designed greatly shortened.

According to a further embodiment, the base plate is assembled at a few mm or cm distance to the bone. This non-contact or low-contact design has the advantage that bone, periosteum or muscle is not compromised below the pate. Since the blood circulation of the bone, of the periosteum or of the muscle below the plate is not to be compromised or only to a small extent, the risk of necroses of the bone and/or muscles below the plate is reduced, and the bones/muscles remain vital and intact, which in turn means that the plate remains fixed in a stable manner. Without necroses, bacterial infection are given no breeding ground and an intact circulation of the bone and/or muscle means that the healing of the osteotomy, at least in the regions in which the osteotomy line runs in the vicinity of the base plate, is not negatively influenced.

Figure 17:
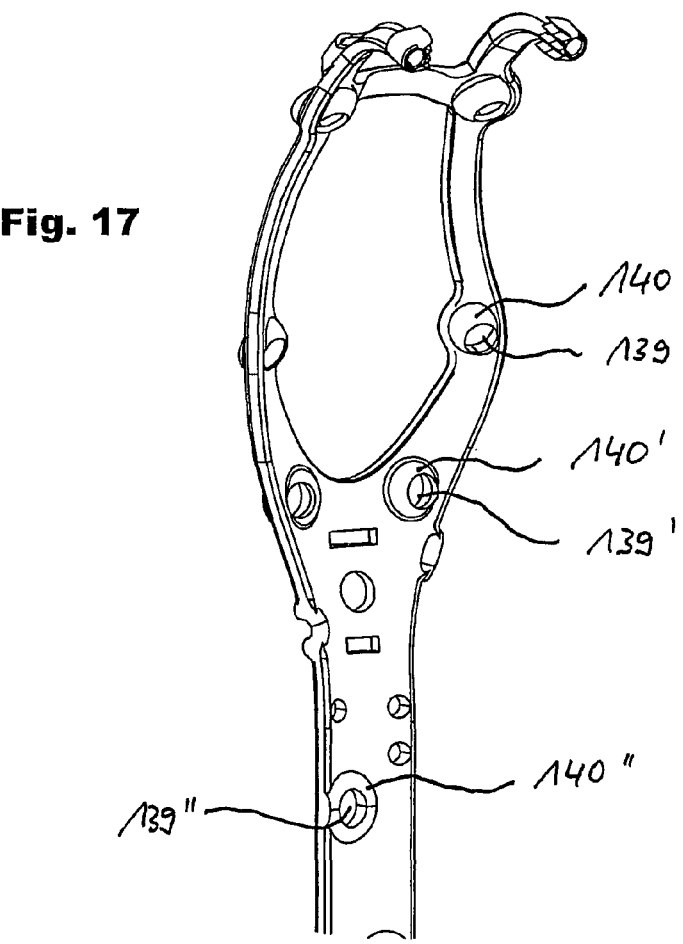
FIG. 17 a detailed enlargement E of the proximal region of the implant according to FIG. 14a, in a view according to FIG. 14e.

For realising the no-contact or low contact design, a plurality of spacer cams are arranged on the side of the base plate, which faces the bone, or spacers 140 are arranged around the screw holes 139 on the same side of the base plate, as is indicated in FIG. 17.

If angularly stable screw systems are applied for the compression of the shank or of the base plate on the femur, or other suitable threaded holes are available, then the distance between the plate and the bone may also be set by way of screwable bolts, as are known as spacers for example of the NCB system of the company ZIMMER. The bolts are rotated into the screw holes/bolt holes before the implantation of the plate, and, depending on the bolt type, permit the setting of variable distances, and if desired, may be removed again after the implantation of the plate.

Generally, for the fixation of the plate shank on the bone, one may say that conventional, non-angularly-stable or angularly-stable/blocking screw systems are suitable for the fixation of the plate shank on the bone. If angularly-stable/blocking screw systems are used, then monoaxial systems with which only one predefined screw direction is possible (e.g. LCP system of the company SYNTHES) or polyaxial screw systems, with which a free direction choice of the screw is possible (e.g. Polyax of the company DEPUY or NCB-system of the company ZIMMER), have been found to be advantageous.

The fixation of the base plates of the implants according to the invention may be realised with monocortical or bicortical screws. One advantage of the monocortical screws lies in the fact that the prosthesis shank or cement casing of the prosthesis shank is not affected by the screw, and thus there is no danger of a loosening of the prosthesis shank. The advantage of the bicortical screws lies in the improved retention. In the case that it should preferred it, or should a fixation with screws not be considered, then one may also fixate by way of cables, wires or straps.

A fixation by way of resorbable or non-resorbable threads is likewise possible, and has the advantage that metallic wear, which may be induced by a loosening of the prosthesis, is avoided.

Figure 19:
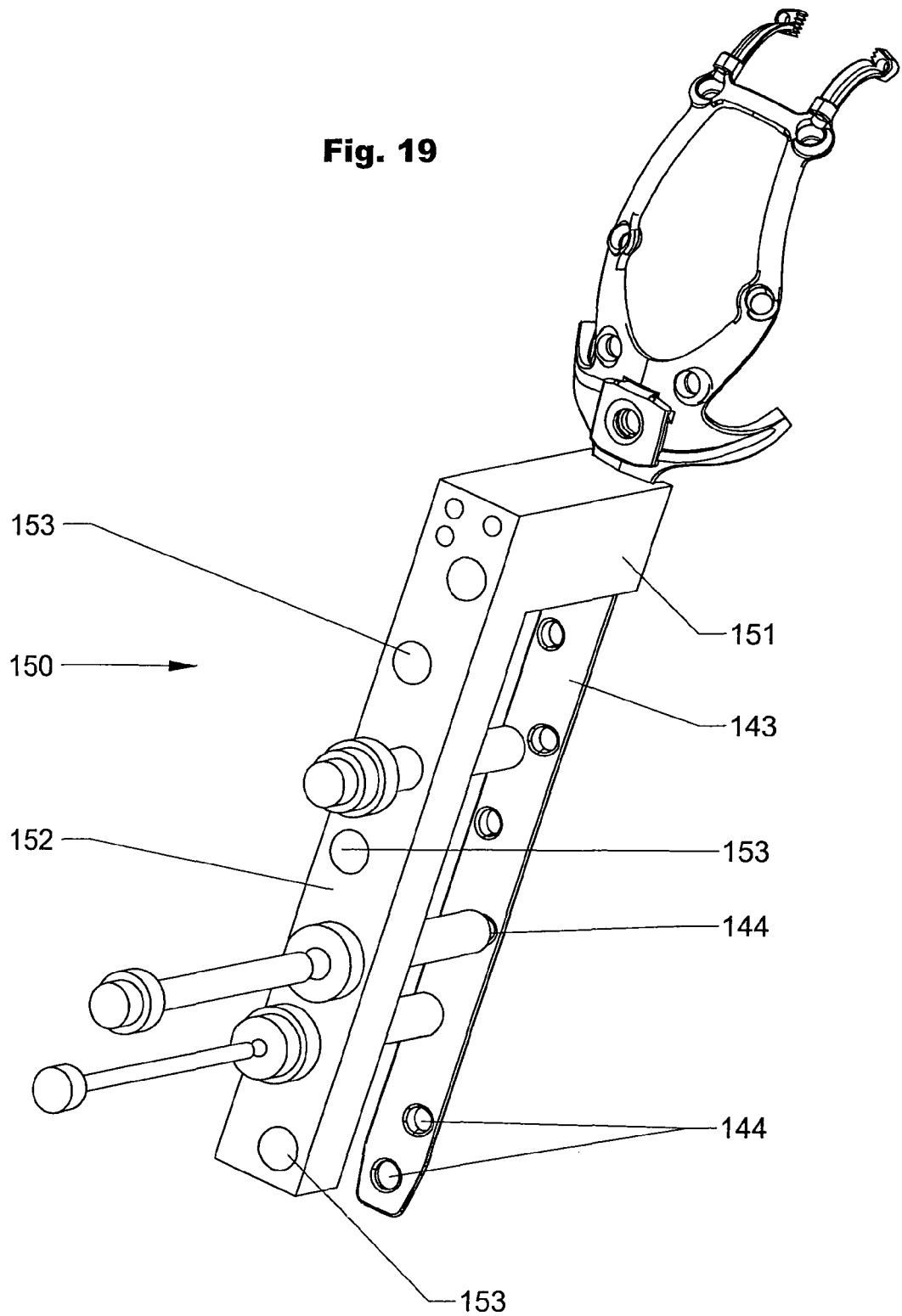
FIG. 19 an implant according to a further embodiment, in active connection with an implantation aid in the form of a target bow, with a plurality of bore-sleeves of a different diameter.

The use of a target bow assembled on the base plate in a temporary manner has been shown to be advantageous, for the minimal invasive implantation of base plates with long shanks, as are represented by way of example in the FIGS. 7 or 14 to 19, and this target bow permits the occupation of the plate holes without opening up the muscle and/or pushing it away. A target bow 150 according to one preferred embodiment together with a base plate 143 according to a further embodiment of the invention, is represented in FIG. 19. The target bow 150 is releasably fastened below the clamping device at the proximal end region of the shank in the figure, so that the base plate 143 with the target bow 150 may be held in a temporary manner and be pushed under the musculus vastus lateralis. The L-shaped target bow with an abaxial piece 151, which is essentially perpendicular on the shank, engages on the shank. A bow arm 152, which is arranged at right angles on the abaxial piece 151, runs in a positional precise manner parallel and distanced to the shank 143, so that angularly stable screws may be introduced through the bow arm 152 of the target bow 150 into screw holes 144 in the plate shank 143, after the tightening of the cable by way of drill sleeves 160. Positioning bores 153 for receiving drill sleeves 160 are arranged in the bow arm 152, corresponding to the screw holes in the plate shank 143. In the embodiment example of FIG. 19, the positioning bores 153 pass through the bow arm 152 essentially in the perpendicular direction towards the shank 143, so that the bores to be created and thus also the fixation screws are aligned perpendicularly to the femur longitudinal axis. If a different angular position of the bores and/or the screws in the bone is required, then the position and the inclination of the positioning bores in the bow arm with respect to the shank may be selected accordingly.

According to a preferred, minimal-invasive implantation method, the cables are pre-arranged in a first step, which means before the insertion of the base plate below the musculus vastus lateralis. In a second step, the base plate is inserted with the help of a target bow, and subsequently the cables are relaxed with a double-sided cable tensioner and are firmly clamped on the base plate by way of the clamping device. The target bow with the drill sleeve set is subsequently used for creating the bores in the bone, and for rotating in the angularly stable screws, and ensures that the fixation is effected in an exactly positioned manner, but the soft part traumatisation is however kept to a minimum. Cerclages with wire or cable around the femur and plate shank are difficult to apply when the target bow is assembled.

If non-angularly-stable screwing is to be applied (i.e. screwing with threads without a thread in the head region), then preferably combination holes are incorporated in the base plate, as are known for example from the LCP systems of the company Synthes. These combination holes have two regions, wherein a screw with a compression effect may be introduced in a first region, or an angularly stable screw may be incorporated in the second region, of the same hole. Both screws may not be implanted simultaneously, but one after the other. If a shank with combination holes is implanted, then accordingly two positioning bores in the target bow are required for each hole, wherein the positioning bore for incorporating the angularly stable screw runs inclined according to the desired angular position.

Particularly preferably, the implants according to the invention or their base plates are fixed by a combination of the techniques described above. Thus for example, monocortical, angularly stable screws (monoaxial or polyaxial) prevent a "windscreen wiper effect" of the plate shank, without affecting the implanted shank of the hip joint prosthesis or its cement casing, and additional cerclages with cables provide additional stability.

It is basically the case that the prongs and wings of the bases plates may be bent beforehand on the part of the manufacturer or be straight. Straight embodiments may be adapted to the conditions at the bone completely according to the wishes of the operator by way of intraoperatively bending. Preferably however, one uses partially or completely pre-bent variants, which not only offer a saving of time during the operation, but in the case of pre-bent prongs, also help the gripping and bone-setting of the trochanter segment. Partially pre-bent variants have been shown to be particularly advantageous in the case of prongs.

The prongs are preferably flexible, and by way of tightening the cables, permit a perfect adaptation to the individual anatomy of the trochanter tip or the trochanter fragment. A high degree of stability may be achieved by way of a closed course of the cable, with which the cables led over the prongs are led further to the lateral-distal, up to the clamping device.

If the intrinsic stability or auxiliary means ensure the guide of the flexible member, then it is sufficient to arrange such a member, for example in the form of a cable, in a medial manner. Accordingly, also only one prong is necessary according to such an embodiment.

Implants with a lateral prong course and a medial cable course have been found to be possible alternatives, but these require more effort during operation and are thus less preferred. Cables which are firmly connected to the base plate, e.g. are soldered or bonded on the medial tip of the prongs, in contrast are a practical alternative to the cables for threading or insertion, which are described above.

According to further embodiments, the medial blocking of the prongs may also be achieved without a medial crossing of the cables, by way of the cables being medially looped through an eyelet, a ring or a clip, so that one may make do without the crossing.

With a further embodiment with a cable and two prongs, the one cable is looped through eyelets at the ends of the prongs or hooks on these, or fixed to this, so that on tightening this cable, as initially envisaged, the prongs bend until they contact one another medially, and both ends of the cable may be fixed on the clamping device in the tensioned condition.

Figure 15:
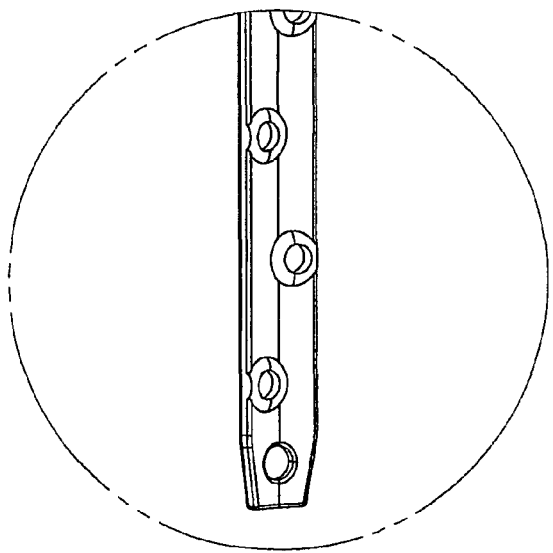
FIG. 15 a detailed enlargement F of the distal shank end of the implant according to FIG. 14a, in a view according to FIG. 14e.

FIG. 15 in a detailed enlargement, shows a pointed shank end which simplifies the insertion of the shank below the M. vastus lateralis, and which may be realised with different embodiments, in particular with implants for minimal invasive implantation.

LIST OF REFERENCE NUMERALS

1 base plate
2 femur
3 lower section
4 upper section
5 surfaced main part
6 narrow limb
7 narrow limb
8 trochanter massif/proximal femur
9 trochanter fragment/trochanter major
10 tuberculum innominatum
11 base body of 6
12 base body of 7
13 surfaced web
15 fossa trochanterica
16 prong
17 prong
18 prong base
19 end portion, thickened continuation
20 holding device
21 flexible member of 41
22 flexible member of 42
23 bore through 19
25 cap on 46
26 elongate extension
27 elongate extension
28 bore through 29
29 exposed end portion of 26/27
30 clamping device
31 clamping plate
32 fine thread screw
33 recesses
36 screws
37 edge
38 lower edge of 5
39 upper edge of 5
41 retainer
42 retainer
43 middle part of the prong regions
44 end-face of 19
45 second run-out of 23
46 end-section of 141
48 end-face of 29
50 fixation devices or cable cerclages
53 cable/elongate and flexible member
54 clamping means
55 cable end/end portion of 53
56 cable end/end portion of 53
57 base body of 54
58 continuous bore in 57
59 continuous bore in 57
60 holder/ring guide
61 cone/base body of 60
62 upper end-face of 61
63 lower end-face of 61
64 casing of 61
65 eyelet
67 groove
68 elongate hole in 81
69 elongate hole in 81
70 ring holder
71 base body of 70
72 hole in 82
73 hole in 82
74 hole in 83
75 free end portion of 76
76 end-face of 71
77 groove
78 elongate hole
79 elongate hole
80 peg
81 upper region of 3
82 middle region of 3
83 lower region of 3
100 base plate
101 plate shank narrow
102 plate shank two-winged
103 longitudinal wing of 102
104 longitudinal wing of 102
105 plate shank wide
106 shank segment
107 shank segment
108 shank segment
109 base plate
110 plate shank
111 wing
112 wing
113 wing
114 base plate
115 prong
116 prong
120 base plate
121 prong
122 prong
123 transverse web
124 thickening
125 thickening
126 guide groove 127 guide groove
128 thickening
129 thickening
130 clamping device
131 shank
132 clamping plate with extensions
133 extension
134 extension
135 through-opening
136 recess/groove
137 inner side
138 inner side
139 screw hole
140 spacer
141 first end portion of 41
142 second/free end portion of 41
143 plate shank
144 screw hole
150 target bow
151 abaxial piece
152 bow arm
153 positioning bore
160 drill sleeve
351 elongate hole in 4
352 elongate hole in 4
353 elongate hole in 4
354 elongate hole in 4
355 screw whole
356 screw hole

What is claimed is:

1. Trochanter retention plate for the refixation of an osteotomised or fractured trochanter major, comprising:
a tension band construction configured to pass via the trochanter major, the tension band construction including:
two retainers configured and operable to refix the osteotomised or fractured trochanter major positively and/or non-positively to the femur,
each retainer including a prong and an elongated flexible member; and
a base plate configured to be fixed to the proximal femur, which is non-positively retained on the femur and serves as the basis of the tension band construction,
the two prongs are proximally arranged on the base plate, the prongs including the elongated flexible members acting on said prongs form the retainers of the closed tension band construction, wherein the prongs extend upward in a proximal direction from the base plate and are arranged at a distance from one another and each prong includes a first end and a second end, the first end being a free end and the second end connected to the base plate, the free end of each respective prong operationally interconnected with the elongated flexible members such that pulling on the elongated flexible members interlocks the free end portions of the prongs with one another amid tension in a region of the fossa trochanterica which increases the intrinsic stability of the tension band construction.

2. The trochanter retention plate according to claim 1, wherein the base plate is designed rigidly, the prongs are designed flexibly, and the elongated flexible members are cables or straps.

3. The trochanter retention plate according to claim 1, wherein a first end portion of the elongated flexible members is connected to the base plate, in the region of the free end portion of the respective prong, and that another end portion of the elongated flexible members runs back to the base plate where it is fixed.

4. The trochanter retention plate according to claim 1, wherein the base plate is configured to be laterally fixed to the proximal femur, the free end portions of the prongs are configured to be interlocked medially of the trochanter major and the elongated flexible members run back to the base plate.

5. The trochanter retention plate according to claim 1, wherein the base plate has a lower distal section and an upper, proximal section which in turn comprises a surfaced main part and, spaced from each other, limbs arranged on said main part which extend in the proximal direction so that the aforementioned components of the proximal section enclose the tuberculum innominatum.

6. A method for the operative refixation of an osteotomised or fractured trochanter major with a trochanter retention plate according to claim 1, comprising: positioning the osteotomised/fractured trochanter major fragment correctly, positioning the plate shank of the base plate on the proximal femur, positioning the tension band construction passing via the trochanter major; through pulling on the flexible, elongated flexible members such that these are bent and the end portions of the two prongs are interlocked with each other so that the osteotomised or fractured trochanter major is refixed positively and/or non-positively to the femur and fastening the flexible, elongated flexible members with their second or free end portions to the base plate through a clamping device.

7. The method according to claim 6, wherein the flexible, elongated flexible members coming from the prongs cross each other above the fossa trochanterica and from there are guided to the base plate where their second or free end portions are held through a clamping device.

8. The method according to claim 6, wherein the elongated flexible members cross each other above the fossa trochanterica immediately after leaving the prongs, from there are guided to the medial circumference of the trochanter massif (calcar femoris) where they cross each other once more and then are guided approximately vertically to the longitudinal axis of the shank back to the clamping device of the base plate.

9. The method according to claim 6, further comprising sliding a base plate with a transverse web following cutting-in of a short component of the origin of the M. vastus lateralis under the same from the top/proximally.

10. The method according to claim 6, wherein a base plate without a transverse web is led around from distal of the origin of the M. vastus lateralis with the upper two plate prongs anterior and posterior of the muscle origin without this having to be cut off.

11. The method according to claim 6, further comprising removably fastening a target bow to the base plate for minimal-invasive implantation.

12. Trochanter retention plate for the refixation of an osteotomised or fractured trochanter major, comprising:
a tension band construction passing via the trochanter major and comprising two retainers operable to refix the osteotomised or fractured trochanter major positively and/or non-positively to the femur,
a base plate configured to be fixed to the proximal femur, which is non-positively retained on the femur and serves as the basis of the tension band construction passing via the trochanter major, and
two prongs proximally arranged on the base plate, the prongs including elongated flexible members acting on said prongs to form the retainers of the closed tension band construction, wherein the prongs have a hook shape and are arranged at a distance from one another and each prong includes a first end and a second end, the first end being a free end and the second end connected to the base plate, the free end of each respective prong operationally interconnected with the elongated flexible members such that pulling on the elongated flexible members interlocks the free end portions of the prongs with one another amid tension in a region of the fossa trochanterica which increases the intrinsic stability of the tension band construction.

\* \* \* \* \*